United States Patent [19]

Coe

[11] 4,375,559

[45] Mar. 1, 1983

[54] PROCESS FOR THE PRODUCTION OF HYDRAZOAROMATICS USING A MULTI-PHASE SYSTEM

[75] Inventor: Charles G. Coe, Macungie, Pa.

[73] Assignee: Air Products and Chemicals, Inc., Allentown, Pa.

[21] Appl. No.: 398,726

[22] Filed: Jul. 15, 1982

[51] Int. Cl.$^3$ .......................................... C07C 109/04
[52] U.S. Cl. .................................. 564/312; 564/311
[58] Field of Search ............................... 564/311, 312

[56] References Cited

U.S. PATENT DOCUMENTS

| | | | |
|---|---|---|---|
| 2,233,129 | 2/1941 | Henke et al. | 564/423 |
| 3,156,724 | 11/1964 | Werner et al. | 564/311 |
| 3,253,010 | 5/1966 | Klauke et al. | 564/311 X |
| 3,260,750 | 7/1966 | Sayigh et al. | 564/311 |
| 3,694,509 | 9/1972 | Rylander et al. | 564/300 |
| 4,217,307 | 8/1980 | Planker et al. | 564/311 |
| 4,326,078 | 4/1982 | Herrmann | 564/312 |

FOREIGN PATENT DOCUMENTS 50-89253  7/1980  Japan.

OTHER PUBLICATIONS

Chemical Abstracts, vol. 16.
Translation of Brand and Steiner Published Paper of 1922.

*Primary Examiner*—Robert V. Hines
*Attorney, Agent, or Firm*—Geoffrey L. Chase; James C. Simmons; E. Eugene Innis

[57] ABSTRACT

A process is disclosed for the catalytic hydrogenation of nitro-alkylbenzenes to hydrazo-alkylbenzenes wherein the reaction is conducted in a two phase solution wherein one phase constitutes an aqueous alkaline base and a second organic phase constitutes a solvent mixture having a first solvent component which is a solvent for the starting reactant and the alkaline base and a second solvent component which lowers the solvent mixture dielectric constant below 25 and which solvent component is a solvent for the reaction product.

17 Claims, No Drawings

PROCESS FOR THE PRODUCTION OF HYDRAZOAROMATICS USING A MULTI-PHASE SYSTEM

TECHNICAL FIELD

The present invention relates to an improved process for the production of hydrazoaromatics from nitroaromatics. Specifically, the present invention is directed to a process which produces improved yields of ortho-hydrazoalkylbenzene and a method for the easy recovery of the ortho-hydrazoalkylbenzene reaction product from the reaction medium.

BACKGROUND OF THE PRIOR ART

The reduction of nitro-alkylbenzene to the corresponding hydrazo compounds is well known in the prior art. The most well known reduction involves the reduction of nitro-alkylbenzenes in the presence of zinc metal and an alkaline media by a batch process. This reduction is not catalytic and therefore consumes large quantities of zinc metal. In addition, the by-products of this reaction produce an environmental problem of disposal of zinc compounds.

Various catalytic processes have been developed for the preparation of aromatic hydrazo compounds. The Germans, in the late ninteenth century, reported the use of a palladium on carbon catalyst in the presence of aqueous potassium hydroxide to produce hydrazobenzene from nitrobenzene. Nitrobenzene and chlorinated derivatives of nitrobenzene have been investigated using catalytic reduction processes.

In U.S. Pat. No. 2,233,129 a process is disclosed for the reduction of ortho-nitrotoluene to a mixture of hydrazotoluene and o-toluidine. The patent discloses that the reaction could be performed in a solvent consisting of an oxygen containing, nonacidic organic compound of from 1 to 7 carbon atoms. The solvent would be utilized in conjunction with an active noble metal catalyst in an alkaline medium. Specifically, the examples show the use of caustic soda and palladium black supported on activated carbon. In addition, the use of an organic solvent such as ethanol was specifically set forth for the production of o-tolidine. However, this recited process generally produces a mixture of hydrazotoluene, ortho-toluidine and certain amounts of azotoluene, rather than a high yield of hydrazotoluene to the exclusion of the other compounds.

The use of aqueous ethyl alcohol solvents for the production of chlorohydrazobenzene has been described in U.S. Pat. No. 3,156,724. The process utilizes noble metal catalysts supported on carbon such as palladium, or platinum and a naphthalene inhibitor such as naphthoquinone. An alkaline reaction medium is provided by the use of sodium or potassium hydroxide. Characteristically, ortho-nitrochlorobenzene is converted to ortho-dichlorohydrazobenzene by catalytic reduction in the above described reaction medium.

The utility of hydrazobenzene compounds such as ortho-hydrazotoluene is documented in U.S. Pat. No. 3,253,010 wherein the hydrazobenzene compounds are reacted with phosgene to create isocyanates which are useful prepolymer components of urethane polymers.

In U.S. Pat. No. 3,260,750 a process for the production of hydrazobenzenes is set forth. The patent sets forth the typical catalysts and reaction media known to date for the production of hydrazobenzenes including, the use of palladium, platinum or rhodium and alcoholic solvents, preferably methanol. Sodium hydroxide is utilized to provide the alkaline medium for the reduction of the nitrobenzene to the respective hydrazobenzene. The patent teaches that the reaction should be conducted in a two-stage process wherein the temperature is controlled from 0° C. to 40° C. in the first stage and from 60° C. to 100° C. in the final stage.

In U.S. Pat. No. 3,694,509 it is disclosed that in a neutral reaction medium using a platinum on carbon catalyst, improved yields of N-arylhydroxyl amines can be obtained in the presence of dimethyl sulfoxide.

In Japanese Patent Publication No. 50-89253, the hydrogenation reduction of nitrobenzenes to hydrazobenzenes is taught wherein a caustic alkali, water, a platinum catalyst, a quinone compound and a small quantity of dispersing agent are placed in a reactor under hydrogen gas and heated for a predetermined time until the reaction is complete.

The prior art fails to provide a process for producing hydrazotoluene compounds in superior high yields in a manner in which the reaction product is easily recoverable.

BRIEF SUMMARY OF THE INVENTION

The present invention discloses a process for the catalytic hydrogenation of nitro-alkylbenzene to hydrazo-alkylbenzene in the presence of a noble metal hydrogenation catalyst, such as palladium, platinum or rhodium unsupported or supported on a carbon base, such as activated carbon or other suitable supports, wherein the process is performed in a two phase solution of a solvent mixture and an aqueous solution of an alkaline base such as an alkali metal hydroxide such as sodium hydroxide or potassium hydroxide. The improvement of the present invention comprises conducting the reaction in a solvent mixture which is inert to hydrogenation in which one solvent component is capable of solubilizing the nitro-alkylbenzene and at least a portion of the alkaline base and another solvent component is effective for maintaining the dielectric constant of the solvent mixture below 25 and is capable of solubilizing the hydrazo-alkylbenzene product.

The reaction medium containing two liquid phases may comprise a first component of methanol, ethanol or propanol and a second component of tetrahydrofuran and the nitroalkylbenzene in one phase and 50% aqueous alkali metal hydroxide as the other phase. The process is further improved by the utilization of a catalytic amount of dimethyl sulfoxide and a hydrogenation inhibiting naphthoquinone, such as 2,3-dichloro-1,4-naphthoquinone. The reaction product is filtered from the solid catalyst and the filtrate is then diluted with an excess of water in order to precipitate the hydrazo-alkylbenzene reaction product for recovery by separation of the solid phase from the liquid phase of the filtrate. This method provides yields of 80 to 90% of hydrazo-alkylbenzene in a manner suitable for continuous processing.

The preferred noble metal catalyst is palladium supported on an activated carbon base.

The preferred alkali metal hydroxide phase is a 50% aqueous solution of sodium hydroxide.

The preferred nitroalkylbenzene is ortho-nitrotoluene which reduces to ortho-hydrazotoluene.

The preferred solvent mixture is methanol and tetrahydrofuran in which methanol constitutes the first component and tetrahydrofuran constitutes the second component.

An alternate solvent mixture is ethanol and tetrahydrofuran in which ethanol constitutes the first component and tetrahydrofuran constitutes the second component.

A preferred quinone inhibitor is 2,3-dichloro-1,4-naphthoquinone.

The present invention process has the advantage of catalytically hydrogenating nitro-alkylbenzenes to hydrazo-alkylbenzenes in high yields with the simple and readily obtained recovery of the reaction product from the reaction medium.

Another advantage of the present invention is the use of a specific novel solvent mixture of methanol and tetrahydrofuran which provides not only processability to the reaction, but also provides unexpected increases in selectivity and yield of hydrazo-alkylbenzene.

It is yet a further advantage of the present invention to utilize a multi-component solvent system constituting one phase of a two phase system in order to provide the proper reaction conditions of alkalinity and dissolution of the reactant and product with ease of recovery of the product from the reaction media.

DETAILED DESCRIPTION OF THE INVENTION

The preparation of hydrazo-alkylbenzenes has been performed by various methods discussed in the prior art as set forth above. However, the present invention provides a unique high yield of hydrazo-alkylbenzene from nitro-alkylbenzene in a multi-phase solution which enhances the specificity of the reaction while providing a uniquely simple method for recovery of the reaction product from the reaction medium. The reaction of the present invention is a hydrogenative reduction reaction of nitro-alkylbenzene. The nitro functional groups of the starting material are reduced so as to be bonded to hydrogen and to one other nitrogen atom. The reduction reaction is carried out until hydrogen consumption ceases. When the consumption of hydrogen drops, the reaction can be terminated. The reaction can be run at hydrogen pressures of up to 100 psig, preferably several atmospheres of pressure.

Catalysts which are used in the hydrogenation of the nitro-alkylbenzene consist of noble metal hydrogenation catalysts which may be supported on inert bases such as carbon. Such hydrogenation catalysts can consist of palladium on carbon, platinum on carbon or rhodium on carbon or other noble metals. Additionally, each of these metals can be used on a different inert substrate such as barium or calcium sulfate or the noble metal catalysts can be supplied and used in their unsupported form. Preferably though, the hydrogenation catalysts would be palladium supported on activated charcoal. The amount of this catalyst which is used in the reaction ranges from 0.001 weight % to 0.1 weight % and is most preferably 0.0146 wt % of the starting material consisting of nitro-aromatic.

In order to prevent or retard the further reduction of the nitro-alkylbenzene to aniline, a hydrogenation inhibitor is provided in the reaction phase. Various quinones are known hydrogenation inhibitors, and it has been found that naphthoquinones selected from the group comprising 2,3-dichloro-1,4-naphthoquinone, 1,4-naphthoquinone, anthraquinone or hydroquinone are good inhibitors for the subject reaction. The preferred quinone inhibitor is 2,3-dichloro-1,4-naphthoquinone. The amount of the quinone inhibitor used in the process can range from 0.01 wt% to 0.20 wt%, with the preferred amount being 0.06 wt%.

Although the inventor does not wish to be bound to a particular theory, the reduction of nitroalkylbenzenes to their corresponding hydrazo compounds is believed to involve the following reaction path with the potential for several competing reactions.

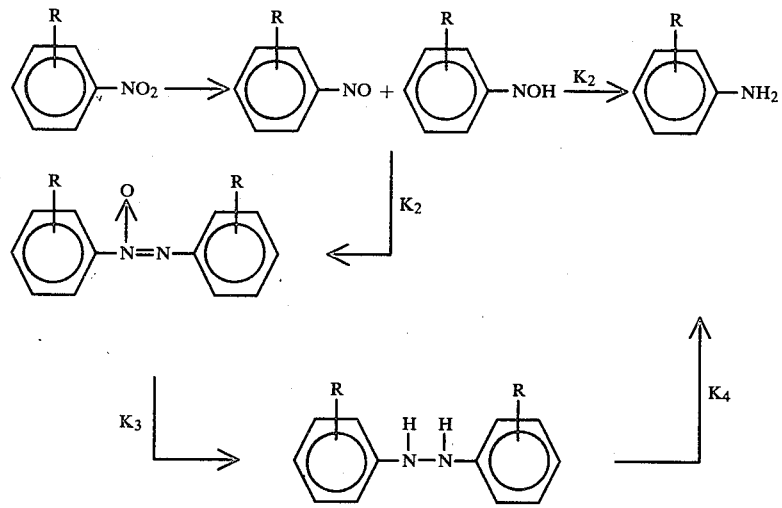

If the reduction reaction is allowed to go to its completion, a fully reduced aniline compound results rather than the desired hydrazo compound. This can occur by either of two paths $K_2$ or $K_4$. Path $K_2$ is a competing reaction which is potentially inhibited by the presence of quinone or base. Path $K_4$ is a reaction which follows the formation of the desired hydrazo compound and is also inhibited by the presence of quinone.

The hydrogenation of nitro-alkylbenzene to hydrazo-alkylbenzene requires a basic reaction medium. This reaction medium, as has been taught in the prior art, is usually an aqueous alkaline base comprising a water solution of an alkali metal hydroxide. The hydroxide can be selected from the group comprising sodium hydroxide and potassium hydroxide. Preferably, a 50% aqueous solution of sodium hydroxide is used in the reaction. The preferred range of the alkaline solution used is from 5 wt % to 50 wt % with the preferred amount being 50 wt %.

The alkaline solution described above comprises the one phase of the two-phase reaction solution of the present invention. The other phase is an organic medium which is a mixture of solvents for the starting material, namely nitro-alkylbenzene. This second phase is unique in that it also has solvent capacity for the reaction product, namely hydrazo-alkylbenzene. This second phase organic solvent mixture is comprised of two miscible solvents utilized together. The solvent mixture can have various specific solvent components, but the particular components selected must be inert to a hydrogenation environment. The solvent mixture of the present invention must have one solvent component which is capable of solubilizing the nitro-alkylbenzene starting reactant, and it must also be able to solubilize at least a portion of the alkaline base. It is believed that the base is retained in the aqueous phase merely as a reserve of such base and that the first organic solvent component solubilizes sufficient base from the aqueous phase to enhance the reaction of the nitro functionality to the hydrazo functionality. The presence of base favors Path $K_1$ over Path $K_2$ of the above-listed reaction network. Because the reactant is soluble in the organic phase, it is necessary that at least one of the solvent components also solubilizes the base because the reaction occurs in that phase.

A second or other solvent component of the organic solvent mixture must be miscible with the first solvent component and is capable of solubilizing the starting reactant, nitro-alkylbenzene. An important and unique aspect of the second solvent component is that is must also be a solvent for the reaction product, hydrazo-alkylbenzene. The inventor has discovered that the second component solvent should lower or maintain the dielectric constant of the solvent mixture below about 25. This control over the dielectric constant of the solvent mixture provides a unique and previously unexpected improvement in the subject reduction process. Although the inventor does not wish to be bound by any particular theory of how the control of the solvent dielectric constant effects the reaction, it is known that a solvent's dielectric constant can drastically alter the rate of electron transfer in homogeneous systems, and it is felt that the selectivity to the reduction product of interest, hydrazo-alkylbenzene, is a result of the relative rate of the undesired reduction ($K_2$ and $K_4$ above) to produce aromatic amines, which is thought to occur by an electron transfer mechanism.

Preferred solvent mixtures include; for the first component, lower alcohols such as methanol, ethanol and propanol and for the second component tetrahydrofuran. The optimal solvent mixture is methanol and tetrahydrofuran, which shows desired selectivity to the hydrazo product and improves processability over other solvent mixtures.

The present invention is unique in providing this two-phase co-solvent reaction medium for the catalytic reduction of nitro-alkylbenzene. The co-solvents operate together to provide solution of the starting material as well as solution of the reaction product thereby preventing crystallization of the desired product on the metal catalyst during the course of the reaction and facilitating the separation of the product in a later step. This allows for a smooth transition through the reaction, as well as providing an easy means for removing the reaction product in a solvent from the solid catalyst material. The present co-solvent system is unique in that respect. Because of this co-solvent system, it has been found that the exact amount of alkaline base supplied in the alkaline aqueous first phase is not critical in that the co-solvent mixture composition, that is the ratio of the first solvent component to the second solvent component, controls the amount of base present in the reaction phase, such that the aqueous phase is simply a reservoir for the base and is supplied as needed to the reaction site by the first solvent constituent of the co-solvent organic phase. In the practice of this process, the amount of organic solvent phase is not critical, provided that there is a sufficient quantity of solvent to completely dissolve the reactant and the product. In practice, it is common to add approximately 10% additional solvent beyond that necessary for dissolution to insure complete solubility of the product at ambient temperatures. In the preferred solvent mixture, the concentration of the tetrahydrofuran to alcohol is in the range of 30 wt% to 80 wt% and the preferred concentration to optimize reaction product yield is 60 wt% tetrahydrofuran.

The catalytic reduction of nitro-alkylbenzenes to hydrazo-alkylbenzene is conducted at a temperature in the range of 25° C. to 100° C., but preferably the temperature is maintained at 60° C. Increasing the temperature above 60° C. reduces the selectivity. The reaction media is blended with a minor amount of a surfactant such as sodium dodecylbenzene sulfonate in order to insure that all of the components are well distributed within the respective multiple phases, that is, an organic phase and an aqueous phase.

The hydrazo-alkylbenzene reaction products produced by the method of the present invention are useful as intermediates for the production of organic dyes, such as azo dyes used in photography. The hydrazo-alkylbenzene is also used as a precursor to isocyanate prepolymer materials.

The production of hydrazo compounds in the solvent system of the present invention can be improved in yield by the addition of a catalytic amount of dimethyl sulfoxide. This catalyst can be used in a range of 0.01 wt% to 5 wt%, preferably 1.0 wt%.

The following examples will further define the process of this invention, but are not deemed to limit the invention thereto.

EXAMPLE 1

A 600 cc autoclave was charged with 60 g tetrahydrofuran, 41 g 95% ethanol, 27.4 g o-nitrotoluene, 17.0 g 50% aqueous sodium hydroxide, 0.80 g 2,3-dichloro-1,4-napthoquinone, 0.40 g 5% Pd on activated charcoal, and 0.40 g sodium dodecylbenzene sulfonate and 1.8 g dimethylsulfoxide. After purging the reactor with hydrogen several times, the reaction mixture was maintained at 60° C. and 60 psig hydrogen while being constantly stirred at 1000 ppm. Hydrogen consumption ceased abruptly after 0.47 moles of hydrogen were consumed. At this point the reactor contents were discharged directly into a tube funnel maintained under a nitrogen atmosphere and separated from the catalyst. The filtrate was added to a two fold excess of water which produced the immediate precipitation of the desired o-hydrazotoluene. Isolation of this product followed by drying under vacuum resulted in the isolation of a 96% yield of o-hydrazotoluene.

EXAMPLE 2

Repeating Example 1 but removing the 2,3-dichloro-1,4-napthoquinone co-catalyst resulted in the production of a 58% yield of solids which contained appreciable amounts of azotoluene and azoxytoluene and was difficult to purify.

EXAMPLE 3

A 600 cc autoclave was charged with 60 g tetrahydrofuran, 41 g 95% ethanol, 27.4 g o-nitrotoluene, 17.0 g 50% aqueous sodium hydroxide, 0.80 g 2,3-dichloro-1,4-napthoquinone, 0.40 g 5% Pd on activated charcoal, and 0.40 g sodium dodecylbenzene sulfonate. After purging the reactor with hydrogen several times the reaction mixture was maintained at 60° C. and 60 psig hydrogen while being constantly stirred at 1000 ppm. Hydrogen consumption ceased abruptly after 0.49 moles of hydrogen were consumed. At this point the reactor was discharged directly into a tube funnel maintained under a nitrogen atmosphere and separated from the catalyst. The filtrate was added to a two fold excess of water which produced the immediate precipitation of the desired o-hydrazotoluene. Isolation of this product followed by drying under vacuum resulted in the isolation of an 83% yield of o-hydrazotoluene.

EXAMPLE 4

The identical reduction of o-nitrotoluene as described in Example 3 was performed only the ethanol was eliminated. This reduction resulted in the isolation of a 48% yield of o-hydrazotoluene. Although the o-hydrazotoluene has a good solubility in tetrahydrofuran, the absence of ethanol prohibits the necessary level of sodium hydroxide from being dissolved in the reactive phase.

EXAMPLE 5

A 600 ml autoclave was charged with 27.4 g o-nitrotoluene, 69 g 95% ethanol, 13.0 g 50% aqueous sodium hydroxide, 0.40 g 5% Pd on activated carbon and 0.40 g 2,3-dichloro-1,4-naphthoquinone. After purging the system several times with hydrogen the reaction mixture was agitated at 1000 rpm and maintained at 60° C. and 60 psig of hydrogen. The hydrogenation continues until absorption of the hydrogen has virtually ceased. At this point, 0.52 moles of hydrogen had been absorbed, the reactor was cooled to 20° C. and immediately discharged into a closed vessel containing 150 cc of water saturated with nitrogen. The diluted mixture was placed in an ice bath for an hour or so to facilitate crystallization. The crude product containing the heterogenous catalyst was collected under nitrogen in a tared fritted tube funnel.

The crude product was dissolved in tetrahydrofuran and filtered away from the catalyst. Addition of water to the filtrate produces a large crop of crystals which are isolated under a nitrogen atmosphere and dried to constant weight under vacuum. The above procedure resulted in an 82% yield of o-hydrazotoluene which has a melting point of 158°–159° C. and is better than 99% pure when analyzed by standard liquid chromatographic methods. An identical reduction using three times as much 2,3-dichloro-1,4-naphthoquinone (1.2 g) resulted in an 83% yield of o-hydrazotoluene whereas removing the quinone produced a 48% yield of hydrazotoluene.

EXAMPLE 6

The identical reduction of o-nitrotoluene as described in example 5 was carried out except 68 g of absolute methanol was used in place of the 95% ethanol. The reduction products were isolated using the same procedures and a 54% yield of o-hydrazotoluene was recovered.

EXAMPLE 7

The identical conditions described in example 3 were carried out except that methanol was used in place of ethanol. After treating the reaction mixture as described in example 3, an 83% yield of o-hydrazotoluene was obtained.

EXAMPLE 8

An identical reduction of o-nitrotoluene as described in example 7 was carried out, except 1.8 g of dimethyl sulfoxide was added to the reaction mixture. This reduction resulted in a 93% yield of o-hydrazotoluene.

EXAMPLE 9

A similar experiment carried out, without the preferred solvent mixture, in a reaction containing two liquid phases produced very different results. In this experiment the autoclave was charged with 27.4 g o-nitrotoluene, 61.5 g water, 19.4 g 50% aqueous sodium hydroxide, 0.4 g 5% Pd on activated carbon, 0.80 g 2,3-dichloro-1,4-naphthoquinone, and 0.40 g of a surfactant, sodium dodecylbenzene sulfonate. After purging the system several times with hydrogen the reaction mixture was agitated at 1000 rpm and maintained at 60° C. and 60 psig hydrogen. The hydrogenation continued until 0.58 moles of hydrogen had been consumed; considerably more than the 0.5 moles required to produce the desired hydrazotoluene. The reactor was discharged into nitrogen saturated water and the crude product isolated in a manner similar to that in Example 5. Only 1.7 g of crude solids were obtained from this reduction. Purification of these solids proved difficult and resulted in the coprecipitation of a mixture of azoxytoluene and hydrazotoluene. The above procedures resulted in a less than 8% yield of impure hydrazotoluene and a large amount of o-toluidine in contrast to the 82% yield achieved in the alkaline ethanolic reaction medium.

EXAMPLE 10

Repeating the procedure of Example 1 and using 60 g tetrahydrofuran, 41 g 95% ethanol, 27.4 g o-nitrotoluene, 17.0 g 50% aqueous sodium hydroxide, 1.0 g 2,3-dichloro-1,4-naphthoquinone, 0.40 g sodium dodecylbenzene sulfonate, 2.6 g 1% Pd on carbon, and 1.5 g dimethylsulfoxide resulted in the production of a 92% yield of o-hydrazotoluene.

EXAMPLE 11

An experiment was run similar to Example 5 in which tetrahydrofuran was deleted from the initial charge, which consisted of 27.4 g o-nitrotoluene, 63 g 95% ethanol, 13.0 g 50% aqueous sodium hydroxide, 0.4 g 5% Pd on carbon, 0.8 g 2,3-dichloro-1,4-naphthoquinone and 5.5 g of dimethylsulfoxide. Eventually after solution of the reaction product with tetrahydrofuran, as in example 5, a 93% yield of o-hydrazotoluene was realized.

EXAMPLE 12

Using the procedure of Example 1 an experiment was run with 1,4-naphthoquinone rather than the dichloro compound. The charge consisted of 60 g tetrahydrofuran, 41 g 95% ethanol, 17 g 50% sodium hydroxide, 27.4 g o-nitrotoluene, 0.5 g 5% Pd on carbon, 0.4 g sodium dodecylbenzene sulfonate and 0.74 g 1,4-naphthoquinone. This run resulted in a 71% yield of o-hydrazotoluene.

EXAMPLE 13

This example was run similarly to the preceding example in that 1,4-naphthoquinone was used as the quinone co-catalyst, but in addition an increase in the concentration of base in the charge was utilized. The charge consisted of 60 g tetrahydrofuran, 41 g 95% ethanol, 32.6 g 50% sodium hydroxide, 27.4 g o-nitrotoluene 0.53 g 5% Pd on carbon, 0.74 g 1,4-naphthoquinone and 0.4 g sodium dodecylbenzene sulfonate. The yield of o-hydrazotoluene was 80%.

EXAMPLE 14

Using the same process as above, the quinone was changed and deletion of dimethylsulfoxide was continued as in the preceding examples. The charge consisted of 60 g tetrahydrofuran, 41 g 95% ethanol, 32.6 g 50% sodium hydroxide, 27.4 g o-nitrotoluene, 0.53 g 5% Pd on carbon, 0.97 g anthraquinone and 0.4 g sodium dodecylbenzene sulfonate. The yield was 82% o-hydrazotoluene.

The results of the preceding experiments are tabulated in the following table.

TABLE I

| | Examples | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| ONT | X | X | X | X | X | X | X | X | X | X | X | X | X | X |
| ETOH | X | X | X | 0 | X | 0 | 0 | 0 | 0 | X | X | X | X | X |
| MEOH | 0 | 0 | 0 | 0 | 0 | 0 | X | X | 0 | 0 | 0 | 0 | 0 | 0 |
| THF | X | X | X | X | * | * | X | X | * | X | * | X | X | X |
| QUINONE | X | 0 | X | X | X | X | X | X | X | X | X | X | X | X |
| SURF | X | X | X | X | 0 | 0 | X | X | X | X | 0 | X | X | X |
| DMSO | X | X | 0 | 0 | 0 | 0 | 0 | X | 0 | X | X | 0 | 0 | 0 |
| NOBLE METAL CATALYST | X | X | X | X | X | X | X | X | X | X | X | X | X | X |
| ALKALINE | X | X | X | X | X | X | X | X | X | X | X | X | X | X |
| YIELD | 96% | 58% | 83% | 48% | 82% | 54% | 83% | 93% | 8% | 92% | 93% | 71% | 80% | 82% |

X = included
0 = omitted
* = added later
ONT = o-nitrotoluene
THF = tetrahydrofuran
SURF = surfactant With reference to the above examples, it is apparent that the novel process of the present invention provides a superior yield and specificity for the production of ortho-hydrazotoluene as well as other hydrazo-alkylbenzenes. The incorporation of dimethyl sulfoxide provides for an increase in yield of, for example from 83% to 96%, of the toluene starting material to the toluene reaction product. This distinction in yield production is obvious from a comparison of Example 1 which includes the use of dimethyl sulfoxide and Example 3 where dimethyl sulfoxide was specifically deleted. Examples 8, 10 and 11 also demonstrate the high yields obtained with dimethylsulfoxide. In a similar manner it can be seen that the naphthoquinone also affects yield in an even more dramatic way. In a comparison of Example 2 wherein the 2,3-dichloro-1,4-naphthoquinone was specifically deleted and Example 1 in which the same quinone was present, a distinction in yield of 58% to 96% respectively is observed. It is apparent that the quinone affects the yield in a significant manner and is very specific to the production of ortho-hydrazotoluene. This specificity is apparent from the other end products which are found when the reaction is conducted in the absence of the quinone such as in Example 2. Other products such as azotoluene and azoxytoluene are found to be produced in addition to the ortho-hydrazotoluene. Therefore, the Examples demonstrate that the dimethyl sulfoxide and a quinone produce a very high yield, upwards of 96%, of the specific end product desired, namely ortho-hydrazotoluene.

The reaction medium is also of critical importance in deriving the desired end product as shown in the preceding examples. Specifically, the use of ethanol or methanol with tetrahydrofuran in the organic phase of the reaction medium is important for obtaining high yields. A comparison of Example 3 wherein ethanol is utilized and Example 4 where the ethanol was specifically eliminated shows that the yield will drop from 83% to 48% when the ethanol is removed from this reaction process. Likewise, when Example 4 is compared to Example 7 wherein methanol constitutes the first component of the solvent mixture, again a yield drop is evidenced in which the methanol run (Ex. 7) had a yield of 83% and the non-alcoholic run (Ex. 4) had a yield of 48%. It is believed that the absence of an alcohol prevents the necessary amount of alkali from being present in the reactive phase, namely the organic phase of the multi-phase reaction. The organic phase of the reaction medium includes as a second component in addition to the alcohol a compound which is a solvent for the reaction product, hydrazo-alkylbenzene. This solvent can be tetrahydrofuran. As can be seen in Example 5, the use of tetrahydrofuran in the typical organic phase of the reaction medium of the present invention does not affect yield, but rather it affects the ease with which the reaction can be taken to its ultimate end, which is the separation of the reaction product from the remaining reactants and reaction medium. As shown in Example 5, when tetrahydrofuran is absent from the reaction site, the reaction still achieves its expected yields, but is difficult to separate from the reaction medium. The subsequent use of tetrahydrofuran on the reaction product in the reaction medium is successful in placing the reaction product in solution for ease of separation with the result of similar yields, namely 82%, as those reactions containing tetrahydrofuran as a starting material in the overall reaction. Therefore, it can be seen that the co-solvents of an alcohol and tetrahydrofuran provide a significant and unique improvement in the reaction process for the production of ortho-hydrazotoluene. The alcohol provides a solvent for the starting material, nitro-alkylbenzene, in which the alkalinity from the aqueous phase is allowed to permiate for the enhancement of the reaction yield, while at the same time the inclusion of tetrahydrofuran provides solubility for the reaction product without degrading the yields from the reaction occurring in the organic phase, the phase in which the tetrahydrofuran exists.

However, it has also been unexpectedly discovered by the inventor that the presence of tetrahydrofuran in the reduction described in Example 7 using methanol significantly improves the yield of the desired o-hydrazotoluene product in comparison to Example 6 which was carried our in a methanolic organic phase without the addition of tetrahydrofuran. This shows that the addition of tetrahydrofuran can not only provide an improved solvent facilitating separation but unexpectedly affects the actual selectivity of the reduction resulting in an increased yield of the desired o-hydrazotoluene product in a methanol system. The large increase in the yield of o-hydrazotoluene was observed only with the addition of tetrahydrofuran to a methanolic organic phase.

In Example 5 where ethanol is employed as the alcohol, the addition of tetrahydrofuran doesn't alter the yield of o-hydrazotoluene significantly. These results were totally unexpected. A possible explanation for the observed difference in selectivity of the reduction obtained by adding tetrahydrofuran to a methanolic medium could be related to the dielectric constant of the solvent mixture. The dielectric constant of the organic phase for the solvent mixture of ethanol and tetrahydrofuran is similar to that for the pure ethanol whereas the dielectric constant for a 60 tetrahydrofuran:40 methanol organic phase is approximately one half the value of that for pure methanol. As discussed previously, it is known that a solvent's dielectric constant can drastically alter the rate of electron transfer in homogeneous systems, and it is felt that the selectivity to the reduction product of interest is a result of the relative rate of the undesired reduction to produce o-toluidine which is thought to occur by an electron transfer pathway.

Therefore, in a methanol system, the addition of tetrahydrofuran can result in altering the selectivity of the reduction as well as acting as an improved solvent system resulting in simpler separations of the product.

Examples 12, 13 and 14 show that the yield of o-hydrazotoluene is not appreciably affected by the specific quinone used as long as some quinone is used in the reaction process.

As has been shown in the several examples above, the present invention provides a reaction medium containing two liquid phases, comprising tetrahydrofuran, a lower alcohol and a nitro-alkylbenzene as one phase and a 50% aqueous alkaline base solution as the other phase. This two phase reaction medium provides a system in which the water of reaction can be easily removed and the product remains soluble in the organic phase so that the solid catalyst can be easily separated from the reaction mixture. After the catalyst has been removed, the product hydrazo-alkylbenzene can be recovered by filtration of the precipitated product which results from the addition of water to the organic phase; or other typical isolation procedures may be used, such as removal of the organic solvent by flash distillation. Using this reaction medium, 80 to 90% yields of ortho-hydrazotoluene have been obtained in a manner suitable for a continuous process design.

Although the present invention has been described in detail with reference to the above examples using o-nitrotoluene, it is believed that one skilled in the art could make various deviations from these specific examples such as the use of other nitroalkylbenzenes without departing from the scope of the invention which is defined by the claims which follow:

I claim:

1. In a process for catalytically hydrogenating a compound of the formula:

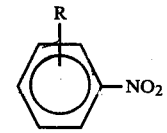

where R is a lower alkyl having one to six carbons, to its hydrazo derivative product in the presence of a hydrogen atmosphere, a metal hydrogenation catalyst, and an alkaline base in aqueous solution, the improvement for enhancing the selectivity and yield of the hydrazo derivative product which comprises utilizing a solvent mixture which is inert to hydrogenation in which one solvent component is capable of solubilizing the compound and at least a portion of the alkaline base and another solvent component which is effective for maintaining the dielectric constant of the solvent mixture below 25 and capable of solubilizing the hydrazo derivative product.

2. The process of claim 1 wherein a quinone inhibitor is present in the reaction phase.

3. The process of claim 1 or 2 including the further steps of filtering the reaction medium to remove the metal hydrogenation catalyst and then diluting the filtrate with water in order to precipitate the hydrazo derivative product for recovery by the separation of the solid phase from the liquid phase.

4. The process of claim 3 wherein the metal hydrogenation catalyst is palladium on activated carbon.

5. The process of claim 3 wherein the alkaline base is an alkali metal hydroxide in a 50% aqueous solution.

6. The process of claim 5 wherein the alkali metal hydroxide is sodium hydroxide.

7. The process of claim 2 wherein the quinone inhibitor is 2,3-dichloro-1,4-napthoquinone.

8. The process of claim 3 wherein the solvent mixture is ethanol and tetrahydrofuran.

9. The process of claim 8 wherein the solvent mixture is in a ratio of 30 to 80 wt% tetrahydrofuran to ethanol.

10. The process of claim 3 wherein the solvent mixture is methanol and tetrahydrofuran.

11. The process of claim 10 wherein the solvent mixture is in a ratio of 60 to 40 wt% tetrahydrofuran to methanol.

12. The process of claim 1 or 2 or 7 wherein a catalytic amount of dimethylsulfoxide is present in the reaction phase.

13. The process of claim 8 wherein a catalytic amount of dimethylsulfoxide is present in the reaction phase.

14. The process of claim 10 wherein a catalytic amount of dimethylsulfoxide is present in the reaction phase.

15. In a process for catalytically hydrogenating o-nitrotoluene to o-hydrazotoluene in the presence of a hydrogen atmosphere, a noble metal hydrogenation catalyst, a quinone and an alkali metal hydroxide in aqueous solution, the improvement comprising conducting the reaction in a solvent mixture of ethanol and tetrahydrofuran and separating the o-hydrazotoluene product from the solvent by filtration of the noble metal catalyst from the solvent and dilution of the solvent with water to precipitate the o-hydrazotoluene product for separation.

16. In a process for catalytically hydrogenating o-nitrotoluene to o-hydrazotoluene in the presence of a hydrogen atmosphere, a noble metal hydrogenation catalyst, a quinone and an alkali metal hydroxide in aqueous solution, the improvement comprising conducting the reaction in a solvent mixture of methanol and tetrahydrofuran and separating the o-hydrazotoluene product from the solvent by filtration of the noble metal catalyst from the solvent and dilution of the solvent with water to precipitate the o-hydrazotoluene product for separation.

17. The process of claim 15 or 16 wherein a catalytic amount of dimethylsulfoxide is present in the reaction phase.

* * * * *